United States Patent [19]

Newkome et al.

[11] Patent Number: 5,376,690
[45] Date of Patent: Dec. 27, 1994

[54] METALLOSPHERES AND SUPERCLUSTERS

[75] Inventors: George R. Newkome; Charles N. Moorefield, both of Temple Terrace, Fla.

[73] Assignee: University of South Florida, Tampa, Fla.

[21] Appl. No.: 116,912

[22] Filed: Sep. 7, 1993

[51] Int. Cl.$^5$ .............................................. C08J 9/00
[52] U.S. Cl. ................................... 521/53; 521/142; 521/152
[58] Field of Search .......................... 521/53, 142, 152

[56] References Cited

U.S. PATENT DOCUMENTS

| | | | |
|---|---|---|---|
| 4,435,548 | 6/1984 | Tomalia | 521/451 |
| 4,507,466 | 3/1985 | Tomalia | 325/451 |
| 4,558,120 | 12/1985 | Tomalia | 528/363 |
| 4,568,737 | 2/1986 | Tomalia | 525/451 |
| 4,587,329 | 5/1986 | Tomalia | 528/363 |
| 4,631,337 | 12/1986 | Tomalia | 528/391 |
| 4,694,064 | 9/1987 | Tomalia | 528/373 |
| 4,737,550 | 4/1988 | Tomalia | 525/419 |
| 5,154,853 | 10/1992 | Newkome | 252/311 |

OTHER PUBLICATIONS

Ringsdorf, "Molecular Architecture/Function of Polymeric Oriented Systems: Models for Study of Org., Surface Recognition and Dynamics of Biomembranes", *Angew Chem Ed. Engl.* 27:113–158 (1988).

Menger, "Groups of Organic Molecules That Operate Collectively", *Angew. Chem. Int. Ed. Engl,* 30:1086–1099 (1991).

Mekelburger et al., "Dendrimers, Arborols, Cascade Molecules: Breakthrough into Generations of New Materials", Angew. Chem. Int. Ed. Engl., 31:1571–1576 (1992).

Tomalia, "Conformational Calculations on Plly--di–n–hexylsilane)" Macromolecules, 20:1167–1169 (1987).

Tomalia, "Starburst Dendrimers. 3.The Importance of Branch Junction Symmetry in the Dev. of Topological Shell Molecules", *J. Am. Chem. Soc.* 109:1601–1603 (1987).

Rengan and Engel, "Phosphonium Cascade Molecules", *J. Chem. Soc. Chem. Commun.* pp. 1084–1085 (1990).

Uchida, "General Strategy for Systematic Synthesis of Oligosiloxanes. Silicon Dendrimers", *J. Am. Chem. Soc.,* 112:7077–7079 (1990).

Wooley, "Polymers with Cont. Molecular Architecture: Cont. of Surface Functionality in Synthesis of Dendritic Hyperbranched Macromolecules" *J. Chem. Soc. Perkin Trans.* 1 pp. 1059–1075 (1991).

Hawker and Frechet, "Preparation of Polymners with Contr. Molecular Architecture: A New Convergent Approach to Dendritic Macromolecules", *J. Am. Chem. Soc.,* 112:7638–7647 (1990).

Hawker and Frechet, "Control of Surface Functional- (List continued on next page.)

*Primary Examiner*—Morton Foelak
*Attorney, Agent, or Firm*—Reising, Ethington, Barnard, Perry & Milton

[57] ABSTRACT

Unimolecular micelles, generally referred to as cascade polymers, are constructed via the addition of successive layers, or tiers, of designed monomers, or building blocks, that possess a predetermined, branched superstructure consisting of connected physical matter inherently defining an internal void volume or void area within the molecular framework. Reactive sites located on the framework and hence within the void regions are capable of being chemically transformed to allow covalent and noncovalent incorporation of one or more guest species into the said void regions. Further, a method is described for making such cascade polymers that includes the steps of forming a unimolecular micelle containing internal void areas with accessible reactive sites capable of bonding to at least one guest after construction of the said unimolecular micelle. The guests are contained within the internal void volume of the cascade polymer and are available and accessible for additional chemical modification.

15 Claims, 7 Drawing Sheets

OTHER PUBLICATIONS ity in Synthesis of Dendritic Macromolecules", *Macromolecules* 23:4726–4729 (1990).

Rajca, "Synthesis of 1,3-Connected Polyarylmethanes", *J. Org. Chem.* 56:2557–2563 (1991).

Rajca, "A Polyarylmethyl Carbotetraanion", *J. Am. Chem. Soc.*, 5889–5890 (1990).

Shahlai and Hart, "Supertriptycene, $C_{104}H_{64}$", *J. Am. Chem. Soc.* 112:3687–3688 (1990).

Pessi et al. "Appl. of Cont-flow Polyamide Method to Solid-phase Synth. of Multiple Antigen Peptide (MAP) based on Seq. of Malaria Epitope", *J. Chem. Soc. Chem. Commun.* pp. 8–9 (1990).

Padias et al., "Starburst Polyether Dendrimers", *J. Org. Chem.*, 52:5305–5312 (1987).

Moore and Zu, "Synthesis of Rigid Dendritic Macromolecules: Enlarging Repeat Unit Size as Function of Generation Permits Growth to Continue" Macromolecules, 24:5893–5894 (1991).

Lakowicz et al., "Time-Resolved Fluores. Anisotropies of Diphenylhexatrience and Perylene in Solvents and Lipid Bilayers Obtained from Multifreq. Phase-Modulation Fluorometry" *Biochem.* 24:376–383 (1985).

Menger et al., "Hexapus, A New complexing Agent for Organic Molecules" *J. Am. Chem. Soc.* 103:5938–5939 (1981).

Saunders and Hepler, "Localization of Membrane-associated calcium following cytokinin treatment in *Funaria* using chlorotetracycline", *Planta* 152:272–281 (1981).

Schore, "Transition-Metal-Mediated Cycloaddition Reactions of Alkynes in Organic Synthesis", *Chem. Rev.* 88:1081–1119 (1988).

March, "Effects of Structure on Reactivity" in *Advanced Organic Chemistry, Reactions, Mechanisms, and Structure*, Third Edition, pp. 237–301 (1985).

Nicalaou et al., "Synthesis and Chemistry of Dynemicin A Models", *J. Am. Chem. Soc.*, 113:3106–3114 (1991).

Nicholas and Pettit, "An Alkyne Protecting Group", *Tetrahedron Ltrs.* Pargamon Press, GB, 37:3475–3478 (1971).

Exon and Magnus, "Stereoselectivity of Intramolecular Dicobalt Octacarbonyl Alkene-Alkyne Cyclizations: Short Synthesis of dl-Coriolin", *J. Am. Chem. Soc.* 105:2478–2480 (1983).

Magnus et al,. "Synthesis of Remarkably Stable Bicyclo[7.3.1]diynene Esperamicin $A_1$/Calicheamicin Y System", *J. Am. Chem. Soc.* 110:6923–6925 (1988).

Nicholas, "Chemistry and Synthetic Utility of Cobalt-Complexed Propargyl Cations", *Acct. Chem. Res.* 20:214–221 (1987).

Bradley et al., "Surface Chemistry on Collodal Metals: High-Resolution Nuclear Magnetic Resonance Study of Carbon Monoxide Adsorbed on Metallic Palladium Crystallites . . . " *J. Am. Chem. Soc.* 113:4016 (1991).

Ketz et al., "Synthesis of Nido-Carborate Containing Thioureas", *Tetrahedron Lett.* 31:4003–4006 (1990).

Miura et al., "Preparation of Carboranyl Porphyrins for Boron Neutron Capture Therapy", *Tetrahedron Lett* 31:2247 (1990).

Akitt, "Quadrupole Relaxation of Boron-11 and Boron-10 Neclei" *J. Org. Chem.* 3:411–414 (1970).

Nemoto et al., "Polyols of a Cascade Type as Water-Solubilizing Element of Carborane Derivatives for Boron Neutron Capture Therapy", *J. Org. Chem.*, 57–435 (1992).

Mittal et al. in *Micellization, Solubilization, and Microemulsions, (1977)*.

Tanford, in *The Hydrophobic Effect: The Formation of Micelles and Biological Membranes* (1980).

Bochkov et al., *Izv. Akad. Nauk SSSR Ser Khim. (USSR) p. 195 (1987)*.

Kim and Webster, *J. Am. Chem. Soc.*, 112:4592 (1990).

Miller and Neenan, *Chem. Soc.* 112:4592 (1990).

Shinkai et al., *J. Am. Chem. Soc.* 108:2409 (1986).

Brooker and Sprague, *J. Am. Chem. Soc.* 63:3214 (1941).

Menger et al., *Am. Chem. Soc.* 103:5938 (1981).

de Gennes et al., *J. Phys. Letter*, 44:351 (1983).

Nicolas et al., in "Transition Metal Organometallics in Organic Synthesis", vol. II (1978).

Tomasik et al., in "Pyridine Metal Complexes" (1985).

Newksome et al., "Building Blocks for Dendritic Macromolecules" *Aldrichimica Acta*, 25:31–38 (1992).

Newkome et al., *Angew. Chem. Int. Ed. Eng.* 30:1176–1180.

Newkome et al., *Am. Chem. Soc.* 103:5938 (1981).
Newkome et al., *J. Org. Chem.*, 47:4116 (1982).
Newkome et al., *J. Org. Chem.* 198:225 (1980).
Newkome et al., *J. Org. Chem.* 54:5105 (1989).

R = CH₂OCH₂C₆H₅
L = (R')₃P; R'=aryl, alkyl

R = CH₂OCH₂C₆H₅

METALLOSPHERES AND SUPERCLUSTERS

TECHNICAL FIELD

The present invention relates to highly-branched molecules possessing a predetermined three-dimensional morphology, referred to as unimolecular micelles. More specifically, the present invention relates to micelles having uses in areas such as radio-imaging, drug delivery, catalysis and other areas.

BACKGROUND OF THE INVENTION

Neat and orderly arrays for micellar systems have been reported,[1,2] and are structurally based on the original work of Vögtle et al., [3a] who delineated "cascade" construction The U.S. Pat. Nos. 4,435,548, issued Mar. 6, 1984; 4,507,466, issued Mar. 26, 1985; 4,558,120, issued Dec. 10, 1985; 4,568,737, issued Feb. 4, 1986; 4,587,329; issued May 6, 1986; 4,631,337, issued Dec. 23, 1986; 4,694,064, issued Sep. 15, 1987; and 4,737,550, issued Apr. 12, 1988, all to Tomalia et al., relate to branched polyamidoamines. The polyamidoamines include a plurality of pendent aminoamide moieties exhibiting properties which are related to linear polyamidoamines from which the branched polymers are derived. These compounds can be characterized as high molecular weight, highly-branched, multi-functional molecules possessing a three-dimensional morphology. Synthetic strategies employed for the realization of such "cascade polymers"[3b] require consideration of diverse factors including the content of the initial core, building blocks, space for molecules, branching numbers, dense packing limits, and desired porosity, as well as other factors.[4] The selection of the building blocks govern the type of branching desired from the core molecule, as well as the technology used to attach each successive layer or "tier" of the cascade polymer.

Applicants have developed a novel method of making cascade polymers, especially those providing a unimolecular micelle consisting essentially of alkyl carbon possessing diverse terminal functionality. Such compounds are disclosed in U.S. Pat. No. 5,154,853 (1992) to applicants.

Further developments of the above-described chemistry by applicants have demonstrated that the unimolecular micellar character permits the initial evaluation of the orderliness and chemistry within a series of specifically designed, spherical macromolecules due to covalently bound assemblies of internal reactive sites.[5,6] Similar dendritic species have been constructed with amide,[4,7,8] ethereal,[9,10] phosphonium,[11] silicone,[12] germane,[13] and aryl,[14,19] inner linkages and functionalities.

Out of all these systems, however, it has been determined that only three systems, thus far created, have the potential to undergo specifically located chemical modification within the inner lipophilic regions thereof. When there is actual space within these regions, these lipophilic regions are termed "void regions". The sum of the "void regions" constitutes the total "void volume" of the cascade polymer. The presently known compounds having such inner void regions capable of covalent modification are the hydrocarbon-constructed cascade intermediates possessing specifically located internal substituents or unsaturated centers, e.g., dialkylacetylenic moieties, set forth in the above-captioned patent to applicants (U.S. Pat. No. 5,154,853), those compounds disclosed by Moore and Xu,[19] that possess rigid polyalkyne spacers, or connectors, between branching centers and are thus prone to incomplete chemical transformations, and hence asymmetry, due to steric interactions, and those compounds set forth in the Tomalia patents set forth above which are amino-branched compounds having short linkages between branch points (thus minimizing void volume) and internal bridging trialkyl substituted nitrogen atoms possessing less than pure $sp^3$ hybridization, making internal nucleophilic substitution difficult.

Critically, applicants have found[6] that the dialkylacetylene moieties of the cascade polymers set forth herein are also specifically located within accessible void regions. Applicants have shown that molecular guest probes, including diphenylhexatriene (DPH), phenol blue (PB), naphthalene, chlortetracycline (CTC), and pinacyanol chloride (PC) can be used as micellar probes to access the infrastructure of such cascade polymers utilizing known chemistry.[20-24]

Applicants' demonstrations of accessibility of void regions to chemical modification has led to the development of the ability to manipulate internal moieties within the spherically symmetrical dendritic macromolecule, after construction, to allow easy incorporation of internally located sensitive and/or reactive groups which otherwise would be difficult to introduce or protect during cascade construction. Specifically, the introduction of metal and metalloid centers at the interior of cascade infrastructures has been accomplished. Such derived compounds, referred to generically as metallospheres, superclusters, unimolecular Metallomicellanes and Nonmetallomicellanes, Metalloidomicellanes, derivatized Micellanes, or Micellanes, can be utilized for drug delivery of various metals and nonmetals, which are presently difficult to deliver in pharmacologically efficacious matters. The use of carrier-metal combinations as pharmacotherapeutic agents has had the problem of not being able to deliver sufficient metal/nonmetal to a site at a sufficiently low dose of the carrier of the metal/nonmetal per se. The present invention provides a means of delivering high concentrations of the metal/nonmetal moiety(ies) to a site at a relatively low dose of carrier (Micellane system).

SUMMARY OF THE INVENTION AND ADVANTAGES

In accordance with the present invention, there is provided a unimolecular micelle including internal "void" areas. The void areas include reactive sites capable of covalent and noncovalent bonding, such as H-bonding to metal and non-metal guests.

The present invention further provides a method of making a cascade polymer, including the steps of forming a unimolecular micelle possessing internal void areas having reactive sites capable of covalent and noncovalent bonding to at least one guest thereby constraining the guest(s) within the void area(s). The guest(s) is (are) contained within the(se) void area(s).

"The file of this patent contains at least one drawing executed in color. Copies of this patent with color drawing(s) will be provided by the Patent and Trademark Office upon request and payment of necessary fee."

BRIEF DESCRIPTION OF THE DRAWINGS

Other advantages of the present invention will be readily appreciated as the same becomes better understood by reference to the following detailed description when considered in connection with the accompanying drawings wherein:

FIG. 1A shows an expanded view of the second tier of a representative Micellane model and various guests and probe molecules;

FIG. 1B shows a contracted view of the second tier of a representative Micellane model;

FIGS. 2A-2D show computational demonstrations of the nonbonded incorporation of various molecular probes within the representative Micellane as illustrated in FIG. 1: wherein FIG. 2A is buckminsterfullerene, FIG. 2B is diphenylhexatriene, FIG. 2C is chlortetracycline, and FIG. 2D is naphthalene;

DETAILED DESCRIPTION OF THE INVENTION

The present invention provides a unimolecular micelle including internal void areas, the void areas including reactive sites capable of covalent and noncovalent bonding to guest(s). The unimolecular micelles of the present invention are cascade polymers which act as micelles. Such unimolecular micelles can be generally in the form of those disclosed in U.S. Pat. No. 5,154,853 to applicants, cited above, being all alkyl molecules, or in the form of those disclosed in the Tomalia patents discussed above, having a nitrogen core. Such compounds have pre-defined branching, depending upon the number of sequential tier additions that are performed in accordance with the above-cited references The etymology of the term "Micelle" as employed in the classical or usual sense, refers to a noncovalently associated collection (aggregate) of many simple molecules functioning as a unit having unique properties (e.g., aqueous solubilization of water insoluble materials) that are not observed with the individual molecules which comprise the micelle; whereas as used herein, unimolecular micelle or micellane refers to a single macromolecule, possessing a covalently constructed superstructure, that can perform the same function(s)[6] as a classical micelle. Additions to these terms denote the incorporation of specific types of metals or nonmetals within the chemically accessible lipophilic interior of the unimolecular micelle. The term ligand is meant to describe any site that has the ability to donate electron density, such as a pair of electrons to a metal or nonmetal moiety, thus forming a covalent or noncovalent bond. Most often the term is used when discussing metals that are bonded, or complexed, to atoms, such as N, P, O, and/or S. The term guest(s) is (are) meant to describe any metal or nonmetal (or any reasonable combination thereof) specie(s) that can be introduced into or onto the cascade framework. The introduction can be irreversible due to the formation of covalent bonds or reversible due to the formation of noncovalent bonds that are easily broken (e.g., hydrogen bonds) or the reversibility may be due to lipophilic-lipophilic and hydrophilic-hydrophilic attractions.

The surfaces of the micelles can be readily coated with metal ions. Mono-, di-, and trivalent metals are being possibly bonded directly or indirectly through terminal carboxyl groups or the like, similar to the dissolution of metal ions by most micellar or acidic systems.

The alkylcarbons surrounded by the branched arms of the micelles define a core therewithin. The above-cited patent discloses the incorporation of single nitrogen, oxygen, sulfur, or phosphorus molecules into the molecular core by non-chemical bonding. That is, the molecules are seated within the void regions of the infrastructure, but not chemically bound therein. It is further possible to incorporate chirality into either the core region or on the surface, thereby creating a chiral sphere with an objectively active surface and/or interior possessing the ability to resolve and recognize chiral molecules.

The above-cited patent discloses that unimolecular micelles made in accordance with the present invention have a porosity which is predetermined, created by the relationships of the branches, the core defined above, and each of the quaternary areas or tertiary centers (carbon core or nitrogen branching sites, respectively) and created by each additional tier layered thereon. The porosity of the inside core can be changed by increasing or decreasing the distances between the quaternary or tertiary centers; that is, by changing the branch arm lengths.

The surface character of the micelles made in accordance with the present invention can also be varied. For example, a carboxyl surface can be created, thereby rendering the micelles useful for detergents and surfactants, and also reactive to pH.[25] Changes in pH which increase the solubility of the surface components can expand the dendritic arms, thereby allowing accessibility to the void regions of the unimolecular micelle. Returning the pH to its original character can then contract the dendritic arms, thereby once again enclosing the void regions. This method of changing solubility of the unimolecular micelles by changing the environment in which the unimolecular micelles are retained can be used to provide accessibility to the void regions for chemical modification, as discussed in detail below.

Besides carboxyl groups, hydroxyl groups, and amines, other acidic, neutral, and/or basic functionalities can be incorporated onto the surface or on interior dendritic arms adjacent to the void regions of these unimolecular micelles as set forth in U.S. Pat. No. 5,154,853. The void areas of these unimolecular micelles made in accordance with the present invention have been characterized. The expanded and contracted nature of such dendritic arms defining the micelles have also been characterized.

Figures 1A, 1B, 2A, 2B, 2C:
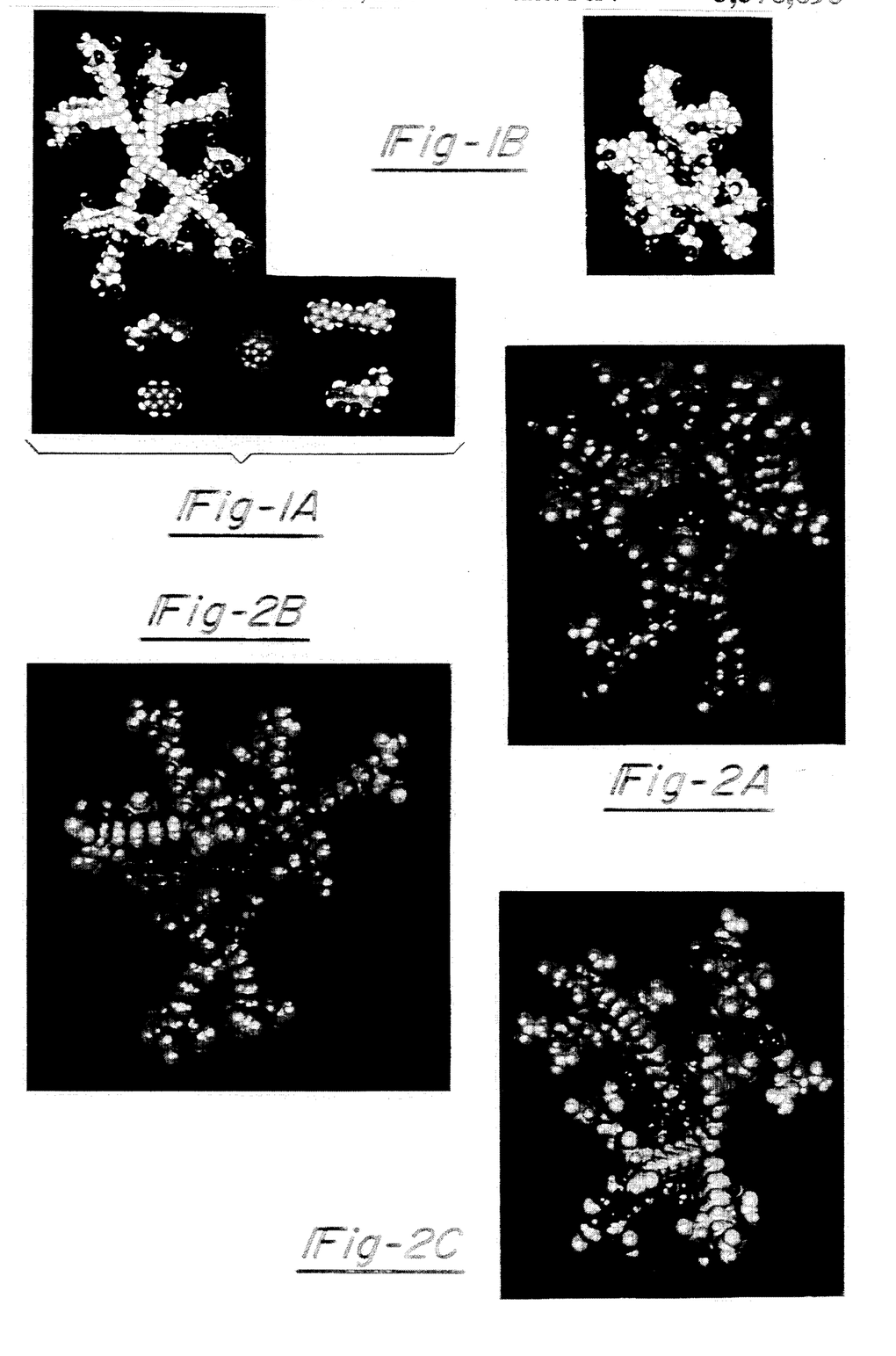

FIG. 1 shows the expanded and contracted views of the second tier of acidic coated unimolecular micelles made in accordance with the present invention, as well as depicting the void regions, and, hence, the total void volume, located within the cascade infrastructure. Nonbonded molecular guests that have been shown to be incorporated include, but are not limited to, diphenylhexatriene (DPH), phenol blue (PB), naphthalene, chlortetracycline (CTC), and/or pinacyanol chloride (PC).

Figure 2D:
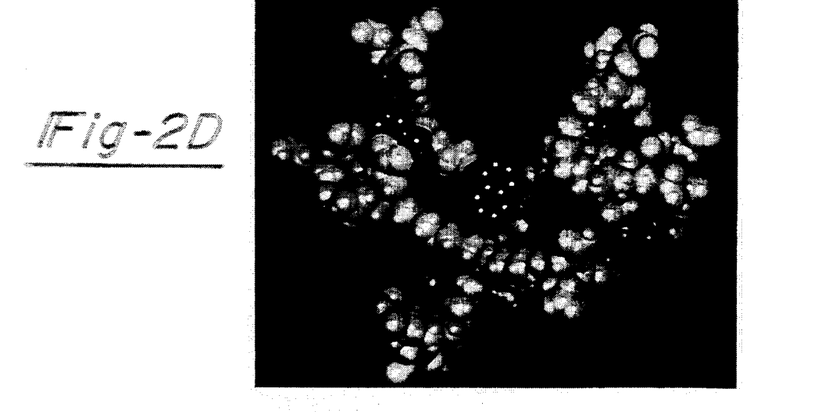

The sizes of the void regions have been demonstrated computationally by the incorporation of a 9 Å $C_{60}$ buckminsterfullerene, as shown in FIG. 2A. As shown, four such spherical guest(s) can be conveniently hosted within the molecule shown in FIG. 1. FIG. 2 further shows other previously used probes to be docked in a partially-expanded molecule as shown in FIG. 1 to demonstrate the porosity of these unimolecular micelles. As tier growth continues, these void areas are incorporated and engulfed, but are not totally filled, such that construction is totally analogous to the growth of a cauliflower, a point previously made by de Genees to describe N-bridged dendritic species.[26]

Figure 3A:
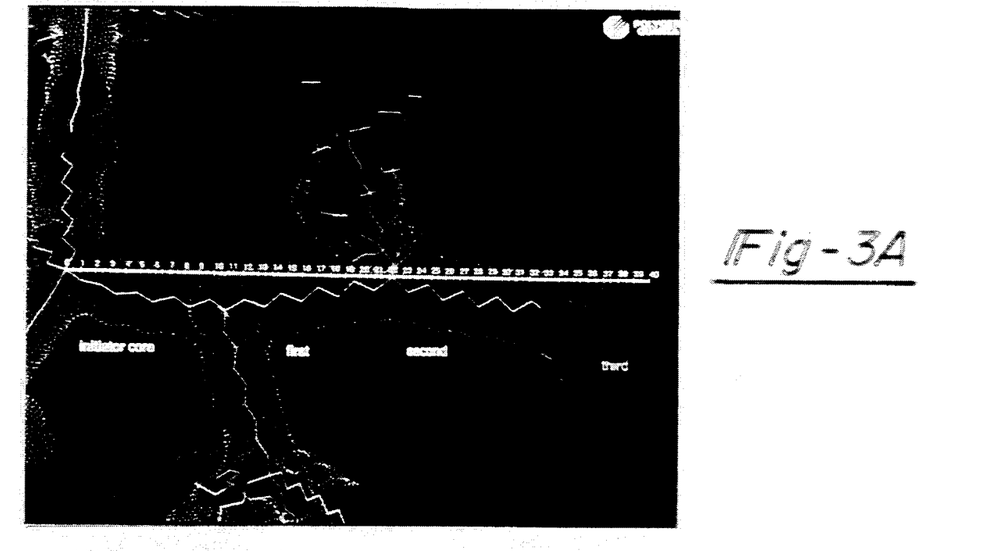
FIG. 3A shows a segment of an extended view of a third tier homolog of the unimolecular micelle depicted in FIG. 1 with a superimposed molecular ruler (divided into units of angstroms (Å))
Figure 3B:
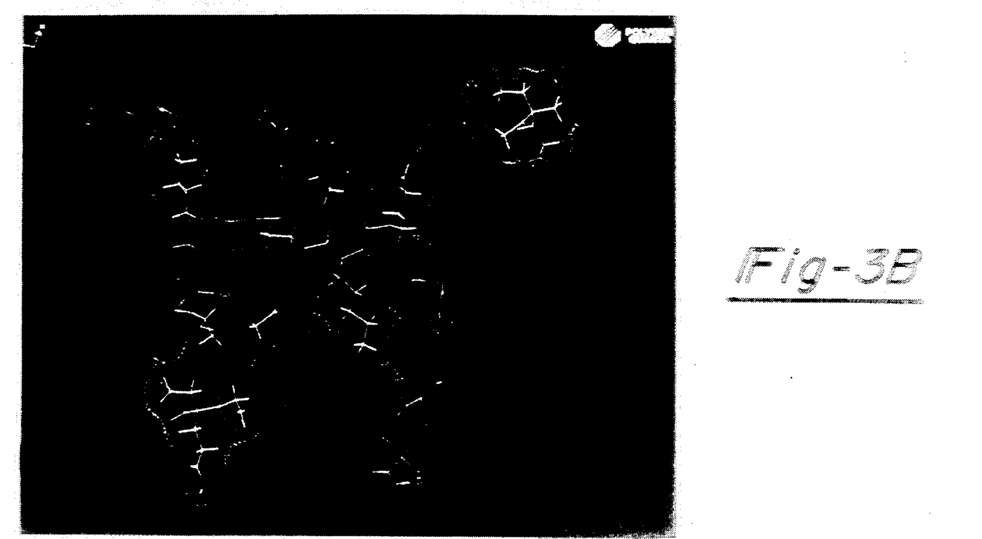
FIG. 3B shows a cross-sectional view of the void volume (holes and crevices) possessed by the homolog.
Figure 4A:
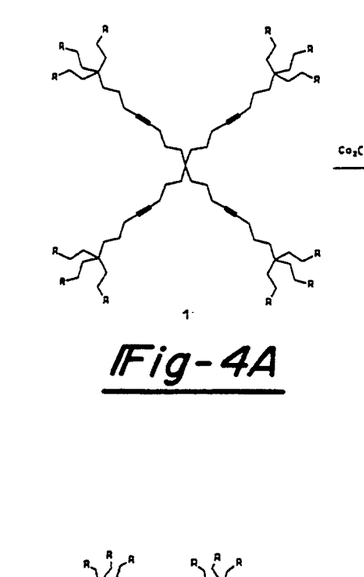
FIGS. 4A and 4C show the preparation of the first tier of a unimolecular Cobaltmicelle.
Figure 4B:
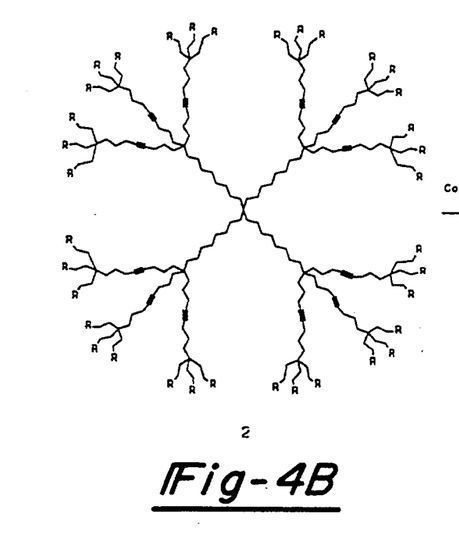
FIGS. 4B and 4D show the preparation of the first tier of a unimolecular Cobaltmicelle.
Figure 4C:
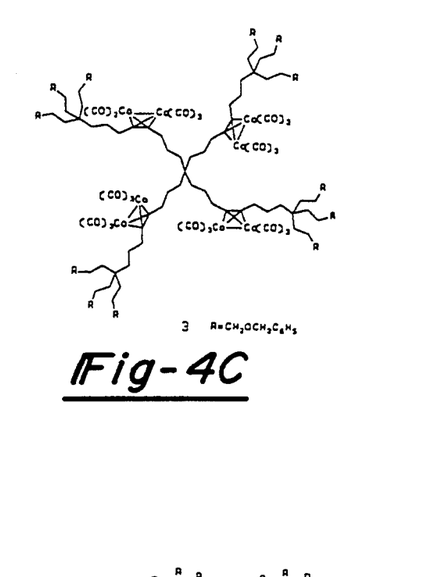
Figure 4D:
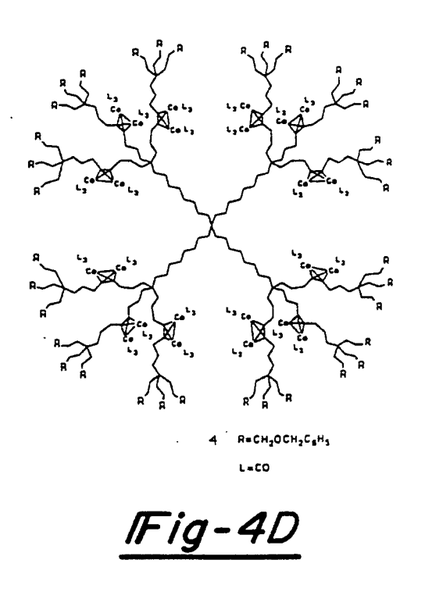
Figure 4E:
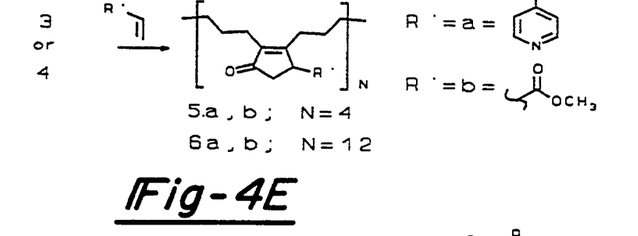
FIG. 4E shows the reactions of the unimolecular Cobaltmicelle with olefins.

The third tier homolog of the unimolecular Micellanoic acid shown in FIG. 1, when viewed from an extended perspective with a depth gauge, reveals a significant void area and an extended radius very near to 40 Å, as shown in FIG. 3. The cross-sectional slice of the contracted conformer exposes holes and cavities within the molecular framework, also shown in FIG. 3.

It has been previously noted in the above-cited patent of the applicants that benzyl protected, unimolecular Micellynoic acids (Formulas 1 and 2) can be heterogeneously and catalytically reduced to afford the corresponding alkanols by Pd-C, ethanol, and tetrahydrofuran. The concomitant hydrogenation of the internal alkyne moieties is straightforward under classical conditions, suggesting branch flexibility and the accessibility of internal functionality to facile chemical modification in accordance with the present invention. Since applicants have shown that there are no signs of "dense packing" at the surface, applicants have discovered accessible reactive sites capable of covalent and non-covalent attachment to guests. In accordance with the present invention, means are provided to manipulate these moieties within the spherical, symmetrical, dendritic macromolecules after construction. This allows for easy incorporation of internally located sensitive and/or reactive groups, which otherwise might be difficult to introduce or protect during cascade polymer construction.

Such reactive sites can be mono-, biand/or tridentate. Examples of monodentate reactive sites are olefins, amines, ethers, sulfides, phosphines, esters, amides, acids, pyridines, ketones, aldehydes, imines, carbenes, and halides. Examples of bidentate sites are acetylenes, pairs of amines, (diamines), pairs of ethers (polyethers), anhydrides, imides, pairs of ketones (diketones), pairs of pyridines (bipyridines), pairs of amides and esters, pairs of sulfides (disulfides), pairs of phosphines, pairs of halides, pairs of carbenes, pairs of acetylenes (diynes), pairs of alkenes (dienes or olefins), thioethers, thioamines, thiophosphines, phosphinoamines, and phosphinoethers. An example of tridentate reactive sites is terpyridines.

The guests can be metallic or nonmetallic ligands bound to at least one of the reactive sites. Examples of incorporated metals, generically known as metal complexes, are cobalt, platinum, copper, palladium, ruthenium, osmium, iron, rhodium, iridium, nickel, silver, and gold. As described below, such metals, if charged, can be bound and captured within void areas of the unimolecular micelles by covalent and/or H-bonding. The chemistry of the present invention allows for capture of such metal ions or clusters in a selective manner within various selected regions of these unimolecular micelles. Thus, hybrid or unimolecular Metallomicelles can be constructed wherein known amounts of various metals can be specifically incorporated into these unimolecular micellar systems to provide desired chemical characteristics to the final product.

For example, cobalt can be covalently bound within the void areas during expansion of the unimolecular micelle and then protected therein by contraction of the micelle, as discussed above. Such cobalt superclusters can be made wherein a single unimolecular micelle can contain a plurality of dicobalt centers, only limited by the number of reactive sites available within the dendritic arms proximate to accessible void regions. Uses of the cobalt superclusters include the mediation of specifically located carbon-carbon bond forming chemical reactions, known as Pauson-Khand reactions.[27] Similar dicobalt complexes are known to undergo reaction with other alkynes and alkenes.

Alternatively, nonmetals can also be incorporated into the unimolecular micelles to form non-metallic superclusters. Such nonmetals can be selected from the group including boron, aluminum, gallium, tin and zirconium. These include nonmetals, generally known as metalloids, which can be used for such applications as the formation of new carbon-carbon bonds.

It should be noted that boron is special in that it can form boron clusters via the propensity of boron atoms to form higher order species. An example of this is the cited (see Experimental Section) reaction of decaborane($B_{10}H_{14}$) with the alkyne reactive sites.

More particularly, the preferred embodiment of the present invention provides a unimolecular micelle consisting essentially of a carbon core atom and essentially all alkyl arms extending therefrom as shown as Formula 2, wherein the R groups can indicate further branching in a quaternary manner. Each quaternary group defines at least four distinct void regions, each of the void regions being substantially lipophilic. As shown, at least one of the void regions includes at least one of the reactive sites, as shown in Formula 2, in the form of an alkyne group. The molecules can include polyalkyne groups in void regions. By known chemistry, these alkyne groups can be derivatized to various functionalities which are mono- bi- and/or tridentate as discussed above.

As discussed above, the outer surface of these unimolecular micelles can be made either lipophilic by the addition of uncharged functionalities on the surface of the micelle or can be hydrophilic by the incorporation of charged or more hydrophilic moieties. Such chemistry is well known in the art.[28]

The present invention further provides a method of making cascade polymers, generally including the steps of forming a unimolecular micelle including internal void areas having reactive sites capable of covalent and hydrogen bonding to guests, and after construction of the micelle, bonding guests to a reactive site in a void area. The ligand is actually contained within the void area, the micelle thereby protecting the guest(s) from the surrounding environment. The amount of these polycomplexes bound within the micelles can be controlled, thereby forming metallo- and nonmetallo-clusters within the unimolecular micelle.

The method of construction of the unimolecular micelles is step-by-step which ultimately results in a fixed, controlled, predictable, and verifiable number of reactive sites (ligands) located at predetermined interior and exterior positions on the cascade polymer. Thus, the number and position of metal and nonmetal species (guests) capable of being incorporated inside, as well as outside, the macromolecular framework is also fixed, controllable, and predictable. Verification of attachment of guests to ligands is readily ascertained via standard spectroscopic techniques, particularly $^1H$ and $^{13}C$ NMR spectroscopies. The number of internally incorporated species is directly related to the size and number of dendritic arms containing predetermined reactive sites. Thus, a first tier, four-directional, unimolecular micelle with four precisely placed internal reactive sites will possess four incorporated species (metals or nonmetals) at precisely located positions. A second tier, four directional, unimolecular micelle with twelve predetermined reactive sites will contain 12 precisely attached guests after reaction, and so on. The relevant point is that the number of attached species is very controlled at specific loci based on our method of cascade construction. Examples are the hydrogenated, polyalcohol intermediates used in the preparation of the Unimolecular Micelles set forth in U.S. Pat. No. 5,154,853 to applicants and the Boron Superclusters and Cobaltomicellanes[29] described in the present application and exemplified below. Even if errors exist due to incomplete transformations giving use to less than pure bimolecular micelle structures, subsequent conversion to the corresponding Metallo- or Metalloid-micellane derivatives will have catalytic activity proportional to the number of internal metal centers.

As discussed above, the unimolecular micelle can be expanded to allow access of metal and non-metal guests or the reactive sites, thereby providing a means of access to the complex center(s) within the void area after construction of the micelle. Upon attaining access to the catalytic site(s),[5] the transient guest(s) is (are) bound to the reactive site and the micelles contracted to contain and protect the transient guest(s). As discussed above, such expansion providing accessibility to one or more of these catalytic sites can be achieved by altering the environment, such as by changing the pH[25] of the external environment solvent or medium. Additionally, these unimolecular micelles having a surface which is more soluble in lipophilic solvents can be transferred to a common organic solvent, such as $CH_2Cl_2$, $CHCl_3$, $C_6H_6$, thereby expanding these lipophilic micelles allowing accessibility. The micelles then are returned to a more hydrophilic solvent causing contraction, due to an inability of the solvent to solvate the surface.[30] This has been demonstrated on classical polymers with organic solvents such as tetrahydrofuran, which causes polymer swelling.

The unimolecular micelles of the present invention can include arms having alkyne moieties. The alkyne moieties can be treated with a metallocarbonyl in an aprotic solvent, the metallo addition being complexed to the internal ligand site(s).

More specifically, the metallo moiety can be selected from the group including, but not limited to, cobalt, platinum, copper, palladium, ruthenium, osmium, iron, rhodium, iridium, nickel, silver, and gold.

The aprotic solvent can be selected from, but is not limited to, the group including $CH_2Cl_2$, $HCCl_3$, $CCl_4$, R—O—R' wherein R and R' are selected from the group consisting of aralkyl and aryl groups, $C_6H_6$ and $CH_3C_6H_5$.

The unimolecular micelles in the present invention can also include polyalkyne moieties. These polyalkyne moieties can have bonded thereto a zero-valent metal under reductive conditions and in the presence of a phosphine donor to the alkyne moieties. The phosphine is thermolysed to generate the zerovalent metal trapped within the void area of the unimolecular micelle.

A further alternative is for the micelle to include arms having bidentate diamino chelate ligands. To produce these compounds, the bonding step discussed above consists of chelating divalent copper to the ligand. Specifically, the bidentate is formed by alkylating a chloro-terminated monomer of the formula:

wherein $R=CH_2OR'$, $CO_2R'$, $CN$ and $CH_2NR_2'''$, $R'=Me$, $CH_2C_6H_5$; ($R''=Me$, Et, pr, bu(t), $CH_2Aryl$ and $R'''=H$, alkyl, aryl, and alkynyl with (2,3, or 4-lithiomethyl-2', 3' or 4'-methyl) bipyridine to form the bidentate diamino of the formula selected from the group consisting of:

These steps can be followed by the subsequent steps of the lithiating of terminal methyl groups and adding further polyhalides to form further internal bi- or tridentate loci in void areas of the unimolecular micelle.

A further alternative is wherein the unimolecular micelle includes arms having polyalkyne moieties, the bonding step discussed above being further defined as treating the alkyne moiety with a acetonitrile activated decarborane moiety.

In accordance with the above methods, bidentate diamino chelate ligand of the formula:

can be made wherein R=H, alkyl, or $CH_2OR'''$ where $R'''=CH_3$, $CH_2C_6H_5$ and $R'=CO_2R''$, $CH_2OH$, $CH_2NH_2$, CN or $CH_2X$ wherein X is a halogen, OMs ($OSO_2CH_3$) or OTs ($OSO_2C_6H_4CH_3$).

The following examples demonstrate the ability of the present invention to provide incorporation into unimolecular micelles of metal and nonmetal centers.

EXAMPLE SECTION

A. Complexes with Cobalt

General Procedure for the Preparation of Cobalt-based Metallomicellanes.

12-Cascade:methane[4]:(5,6-hexacarbonyldicobalt-)nonylidyne:(2-oxapentyl)benzene.

[First generation Cobaltomicellane]

A solution of $CH_2Cl_2$ (10 mL), tetraalkyne-dodecabenzyl ether {12 Cascade:methane[4]:(5,6-yn)nonylidyne:(2-oxapentyl)benzene(0.5 g) and octacarbonyldicobalt (0.30 g,0.89 mmol) was stirred for 12 hours under a $N_2$ atmosphere at 0° C. The solvent was removed in vacuo and the residue was subjected to nonaqueous reverse phase chromatography ($C_6H_6$) to afford (88%) the octacobaltdodecabenzyl ether as a viscous red oil:

13C NMR δ 22.8 ($\underline{C}H_2CH_2O$), 25.6 [$Co_2(CO)_6C_2\underline{C}H_2CH_2$], 32.6 ($CH_2\underline{C}H_2CH_2O$), 34.0 [$Co_2(CO)_6C_2\underline{C}H_2$], 36.4 [$C_4\cdot$, $Co_2(CO)_6C_2\underline{C}H_2\underline{C}H_2CH_2$], 71.2 ($\underline{C}H_2OCH_2C_6H_5$), 72.8 ($O\underline{C}H_2C_6H_5$), 127.3, 127.4, 128.3, 138.6 ($\underline{C}_6H_5$), 201.0 ($\underline{C}O$); 1H NMR δ 0.60-2.70 [br m, $(CH_2)_3Co_2(CO)_6C_2(CH_2)_3C\{CH_2CH_2\}_3$, 96 H], 3.40 (br s, $CH_2O\underline{CH_2}C_6H_5$, 24 H), 4.46 (br s, $\underline{CH_2}C_6H_5$, 24H), 7.30 (br s, $C_6H_5$, 60 H); IR (neat) v=3075, 2940, 2870, 2085, 2044, 2015, 1280, 1100, 745 cm$^{-1}$ 36-Cascade:methane[4]:nonylidyne:(5,6-hexacarbonyldicobalt) nonyliayne:(2-oxapyntyl)benzene.

[Second generation Cobaltomicellane]

13C NMR δ 22.8 ($\underline{C}H_2CH_2O$), 23.5 [$\underline{C}H_2(CH_2)_4CH_2$]29.7 [$(CH_2\text{ })_3CH_2CH_2(CH_2)_3$], 25.7 [$\overline{C}o_2(CO)\ \ 6C_2CH_2CH_2\ \ $], 32.6($CH_2\underline{C}H_2CH_2O$), 34.0 [$Co_2(CO)_6C_2\underline{C}H_2$], 36.4 [$C_4\cdot$, $Co_2(CO)_6C_2CH_2CH_2CH_2$], 36.7 [$\underline{C}H_2(CH_2)_6CH_2$]71.2 ($\overline{C}H_2OCH_2C_6H_5$), 72.8($O\underline{C}H_2C_6H_5$), 127.3, 127.4, 128.3 138.6($\underline{C}_6H_5$), 202.0($\overline{C}O$); 1H NMR δ 0.60-2.70 [br m, $(\overline{C}H_2)_8$, $(CH_2)_3Co_2(CO)_6C_2(CH_2)_3C\{CH_2CH_2\}_3$, 356 H], 3.42 (br s, $CH_2O\underline{CH_2}C_6H_5$,72 H), 4.46 (br s, $\underline{CH_2}C_6H_5$, 72H), 7.30 (br s, $C_6H_5$, 180 H) ; IR (neat) v=3075, 2940, 2870, 2085, 2044, 2015, 1280, 1100, 745 cm$^{-1}$ The reactivity within the lipophilic core of these unimolecular micelles was conducted via treatment of the internal alkyne moieties of Formulas 1 and 2 with $Co_2(CO)_8$[31] in an aprotic solvent such as $CH_2Cl_2$, shown in FIG. 4. Dicobaltoctacarbonyl is well known to form additional complexes to acetylenes and has been successfully employed for their protection.[31] These resultant dicobalt complexed alkynes act not only as protecting groups but also promote ene-yne cyclopentenone cyclization,[32] thus affording entry to a novel series of carbocyclic substituted micelles via chemical modification of their internal lipophilic region. Substituents attached to the guest alkene allow precise placement of diverse functionality within one or more of the micellar void volume regions.

The information of functionalized terminal alkene guests is envisioned via the formal 2+2+1 cyclization. Thus, treatment of cobalt superclusters Formulas 3 or 4 (FIG. 4) with 4-vinylpyridine or methyl acrylate should afford Formulas 5a,b or 7a,b (FIG. 4). Benefits of the transformation include the incorporation of α,β-unsaturated carbonyl moieties and precisely anchored reagents which can be used to ascertain an accurate "depth of reagent" inside the inherent cavities in these derivatized unimolecular micelles. Insight also is afforded into the regiochemistry of the cyclizations.[35] The nature of the reagents environment (i.e., hydrophobicity, lipophilicity, mobility, density, etc.) can then be related to that observed for classical micelles.[2]

Isolation and purification of the $Co_2(CO)_6$ intermediates has been reported[32] generally not to be required prior to ene-yne cyclization due to high conversions. Treatment of the tetraalkyne Micellane (Formula 1) with dicobaltoctacarbonyl affords ($\simeq$100%) the deep red, viscous dicobalthexacarbonyl adduct (Formula 3). Formation was evidenced by the appearance of 13C NMR resonances at 200.3 (C≡O) and 99.6 ppm [$C_2(Co_2(CO)_6]$, as well as the disappearance of signals at 80.1 and 19.3 ppm attributed to the C≡C and α-$CH_2$ precursor moieties, respectively. Further support was provided by the symmetry of the 13C NMR spectrum and severe broadening of the 1H NMR spectrum, and an IR absorption at 2000 cm$^{-1}$.

4-Dicobalt clusters were attached at four discrete loci at a distance no greater than 6.4 Å[36] from the core atom. Similar 1H and 13C NMR spectral signals are observed when the dodecaalkyne derivatized Micellane (Formula 2) is treated with $Co_2(CO)_8$ to afford the dodecadicobalt supercluster (Formula 4). As each tier is added, the number of internal alkyne sites increases (4→12→36→108 . . . ), thus placing each set of alkyne centers at a discrete distance from the core (6.4, 17.3, 28.4, and 37.4 Å, respectively); each center available for subsequent complex formation. Since the dicobalt clusters are protecting groups for the alkyne moiety, the initial 4 clusters at 6.4 Å were maintained during construction of the next tier. Addition of twelve equivalents of $Co_2(CO)_8$ will afford a micellar species with 16-dicobalt clusters. This procedure can be repeated with added tiers affording 52 (4+12+36)- or 160 (4+12+36+108)-dicobalt cluster centers within the hydrophilic surface coat.

One is not limited to a single metal source. Each tier can incorporate different metal ions or clusters. Thus, the initial 4-dicobalt clusters at tier 1 can be covered by 12-Pt(0) (next section) sites at tier two. Since each tier is constructed independently of the preceding layer, numerous possibilities are conceivable and attainable, provided the chemical stability is maintained during the attachment of subsequent tiers.

B. Complexes with Platinum

Figure 5A:
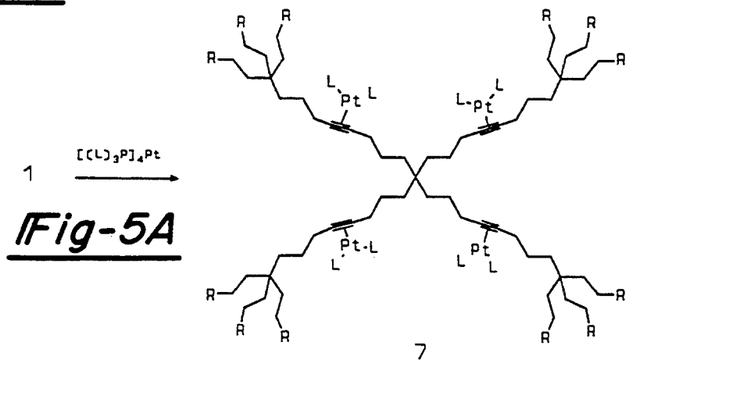
FIGS. 5A-5B show the preparation of a unimolecular Platinomicelles, which possess multiple platinum centers within the lipophilic core.
Figure 5B:
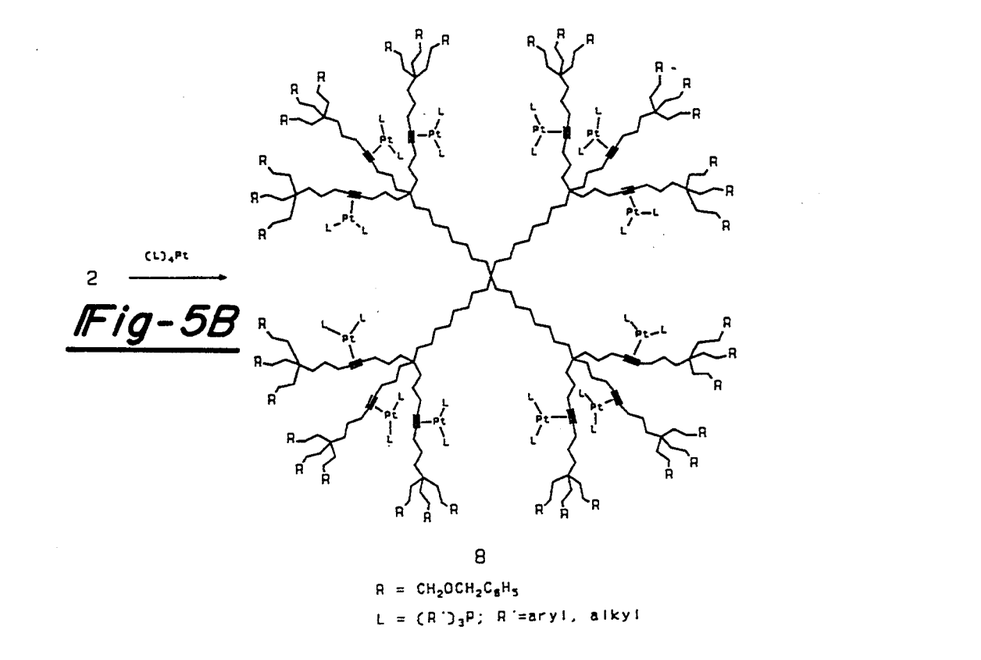

The incorporation of moieties into dendritic "void regions" includes the incorporation of zero-valent metals, such as Pt(0).[37] Thus, the utilization of Pt(O), generated from $K_2PtCl_4$ under reductive conditions (NaBH$_4$·EtOH) in the presence of $R_3P$ (R=alkyl, aryl or aralkyl) leads to platinacycles (Formulas 7 or 8), depending on the size and number of unsaturated centers, as noted above, of the unimolecular micelle (FIG. 5). As the tiers are added, the cavities are eventually sealed (onset of dense packing). However, they are still porous due to the facile molecular motion of the surface functionality at ambient and above temperatures. Thus, thermolysis of the platinocycles within the metallospheres liberates irreversibly the volatile $R_3P$ ligands to generate Pt(0)[37] metal atoms trapped within the inner lipophilic microenvironment.

Examination of these Metallomicelles can be expanded to include the preparation of poly-Pd(0) adducts. Although these palladiocycles are less stable towards external parameters, such as oxidation and heat, they exhibit chemistry similar to their platinum counterparts.[31]

The generation and migration of metal(O) species within inert hydrocarbon pockets affords small, e.g. Pt(0)$_n$, clusters. The mobility within a single pocket affords at least four similar Pt(0)$_n$ cluster centers, but if inter-region migration occurs, a "colloidal transition metal cluster"[38] is possible. Other platinum family metals can be incorporated via similar technology.[38] If intracavity migration occurs, the cluster is limited to a fixed number of metal atoms, and each cluster and symmetry is retained; whereas, if intercavity metal atom migration occurs, cluster size is variable and molecular dissymmetry of the metallomicelle results.

C. Complexes with Copper

Copper-based "metallomicelles" have been shown by Menger to significantly enhance the rate of phosphodiester hydrolysis [e.g., nerve agent GD; (RO)$_2$POF] by as much as $10^6$ due to increased electrophilicity created by constrained metal centers.[2] Introduction into the cascade of a suitable Cu$^{2+}$ ligand leads to copper-based metallospheres that possess this capability.

Figure 6A:
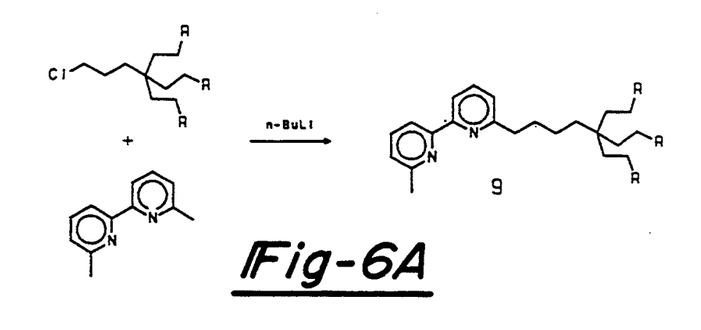
FIGS. 6A-6B show the synthesis of a representative copper-based unimolecular Metallomicelle.
Figure 6B:
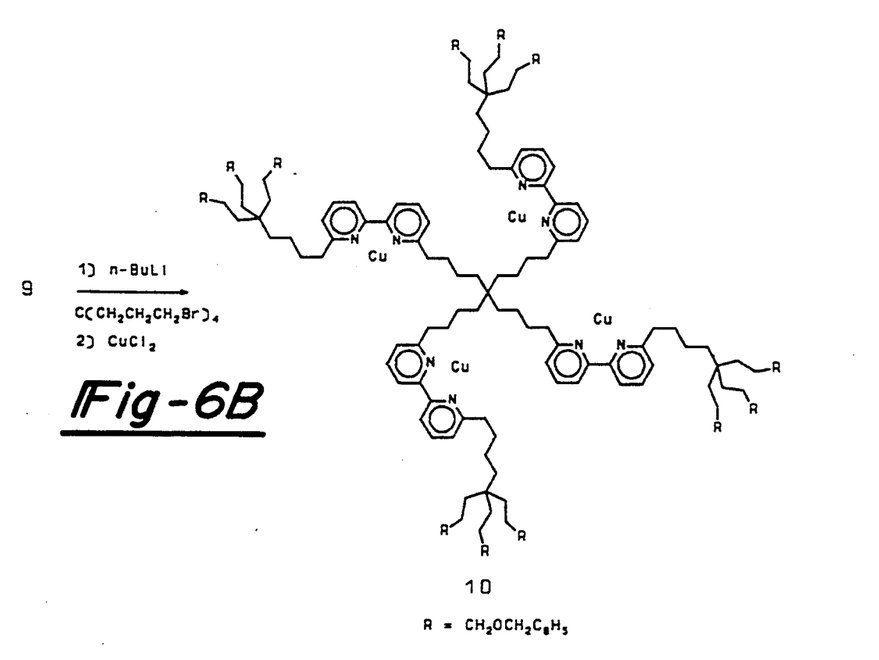

Copper-based metallomicelles are constructed from novel cascade building blocks that incorporate bidentate diamino ligands. Alkylation of the chloro-terminated monomer [4-(3-chloropropyl)-4-(3-benzyloxypropyl)-1,7-dibenzyloxyheptane][5] with (2-lithiomethyl-2'-methyl)bipyridine[39] easily affords a rigid building block (Formula 10) with the requisite chelate site. Since selective metallation has been demonstrated,[40,41,42] subsequent lithiation of the remaining terminal methyl group and addition of a poly-halide core[5] (e.g., 4, 12, or 36 terminal halides, etc.) provides a series of cascade infrastructures (Formula 11) possessing these internal bidentate loci (FIG. 6). Although copper inclusion is shown, this technique can be applied to many other metal ions.[43]

D. Boron Clusters

General Procedure for the Preparation of Boron Superclusters.

12-Cascade:methane[4]:5,6-(1,2-dicarba-closo-dodecarborane)nonylidyne:(2-oxapentyl)benzene.

[First generation boron supercluster]

A solution of acetonitrile (1.0 mL) and excess decaborane (0.3 g, 2.4 mmol) was stirred at 25° C., under a $N_2$ atmosphere, for 30 min. Subsequently, a mixture of toluene (7.0 mL) and the tetraalkyne-dodecabenzyl ether {12-Cascade:methane[4]:(5,6-yn)nonylidyne:(2-oxapentyl)benzene} (0.5 g, 0.22 mmol) was added. After refluxing for 24 hours, MeOH (5.0 mL) and 10% HCI (1.5 mL) were added and reflux was continued for another 12 hours. Upon cooling to 25° C, the solvent was removed in vacuo, $CH_2Cl_2$ (50 mL) was added and subsequently washed with 10% $Na_2CO_3$ (2×50 mL) and saturated brine (2×50 mL), and dried (NaSO$_4$). Concentration in vacuo followed by non-aqueous reverse phase chromatography (10:0.1 v/v $C_6H_6$:EtOAc) afforded (92%) the pure tetra-1,2-dicarba-closo-dodecarborane supercluster: $^{13}C$ NMR δ 23.5 ($B_{10}H_{10}C_2\underline{C}H_2CH_2$ $\underline{C}H_2CH_2O$), 29.6 ($B_{10}H_{10}C_2\underline{C}H_2$), 32.4 ($\underline{C}H_2\underline{C}H_2CH_2O$), 36.5 ($C_4$·,$B_{10}H_{10}C_2\underline{C}H_2CH_2CH_2$), 71.2 ($\underline{C}H_2O$), 72.8 ($O\underline{C}H_2C_6H_5$), 127.3, 127.4, 128.3, 138.6 ($\underline{C}_6H_5$); $^1H$ NMR δ 0.85–2.10 [m, $(CH_2)_3B_{10}H_{10}C_2(CH_2)_3C\{CH_2CH_2\}_3$, 136 H], 3.40 (br s, CH$_2$O, 26 H), 4.46 (br s, O$\underline{C}H_2C_6H_5$, 24H), 7.30 (br s, $C_6\underline{H}_5$, 60 H); $^{11}B$ NMR ($^1H$ decoupled δ–19.6(s, $\underline{B}_{3,6}$), 0.5 (m, $\underline{B}_{4,5,7,11}$), 23.6 (s, $\underline{B}_{8,10}$), 35.6 (br s, $\underline{B}_{9,12}$); $^{11}B$ NMR ($^1\overline{H}$ coupled) δ–19.6 (d, $\underline{B}_{3,6}$, J=145.2 Hz), 0.5 (m, $\underline{B}_{4,5,7,11}$), 23.6 (d, $\underline{B}_{8,10}$, J=119.5 Hz), 35.6 (br s, $\underline{B}_{9,12}$);IR (neat) v 3080, 3030, 2920, 2860, 2575, 1100, 745, 700 cm$^{-1}$.

36-Cascade:methane[4]:nonylidyne:5,6-(1,2-dicarba-closo-dodecarborane)
nonylidyne:(2oxapyntyl)benzene.

[Second generation boron supercluster]

The experimental procedure is the same as that described for the first generation, 12-Cascade, boron supercluster. $^{13}C$ NMR δ 22.5 [C(CH$_2$CH$_2$)$_4^{int}$], 23.5 [C(CH$_2$CH$_2$)]$_4^{ext}$, CH$_2$ CH$_2$O, 29.0 [C(CH$_2$CH$_2$CH$_2$CH$_2$)$_4^{int}$], 29.5 ($B_{10}H_{10}C_2\underline{C}H_2$) , 31 5 [C(CH$_2$CH$_2$CH$_2$)$_4^{int}$], 32.6 ($\underline{C}H_2CH_2CH_2$)), 36.6 [m, $C_4$·,$C_4$·$(\underline{C}H_2)_4$], 71.3 ($\underline{C}H_2O$), 72.8 ($O\underline{C}H_2C_6H_5$), 127.3, 127.4, 128.3, 138.6 ($\underline{C}_6H_5$); $^1H$ NMR δ 0.70–2.15 [br s, $(CH_2)_8^{int}$, $(CH_2)_3B_{10}H_{10}C_2(CH_2)_3C\{CH_2CH_2\}_3^{ext}$, 372 H], 3.41 (br s, CH$_2$O, 72 H), 4.47 (br s, O$\underline{C}H_2C_6H_5$, 70 H), 7.30 (br s, C$_6\underline{H}_5$); 180 H); $^{11}B$ NMR ($^1\overline{H}$ decoupled) δ–19.6 (s, $\underline{B}_{3,6}$), 0.5(m,$B_{4,5,7,11}$), 23.6(s,$\underline{B}_{8,10}$), 35.6 (br s, $B_{9,12}$); IR(neat) v=3080, 3030, 2920, 2860, 2575, 1100, 745, 700 cm$^{-1}$.

Synthesis of water-soluble boron clusters to be used in cancer treatment, specifically, boron neutron capture therapy, has been the subject of recent investigations.[44] Localization of high concentrations of boron, provided by 1,2-dicarba-closo-dodecarboranes (o-carboranes), at tumor sites and subsequent neutron activation results in the decay of $^{10}B$ (20% natural abundance) to an o-particle and $^7Li$ which interferes with cancer cell replication. Aqueous solubilization has thus far relied on transformation of $B_{10}H_{10}$ closo-structures to ionic $[B_9H_{10}]^-$ nido-structure,[44a,b] or attachment of a single o-closocarborane to a small, water-soluble delivery molecule.[44c] These methods lack the advantage of delivery of a maximum amount of boron with a minimum dose. Water-soluble polycarborane cascades would circumvent this limitation.

Figure 7A:
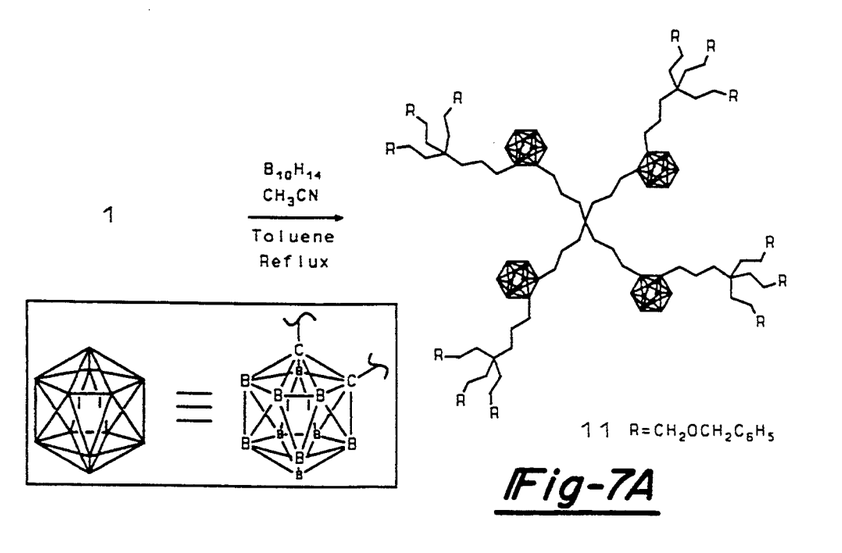
FIGS. 7A-7B show the preparation of the first and second tier unimolecular Carboranomicelles possessing four and twelve internal ortho-carborane moieties, respectively.
Figure 7B:
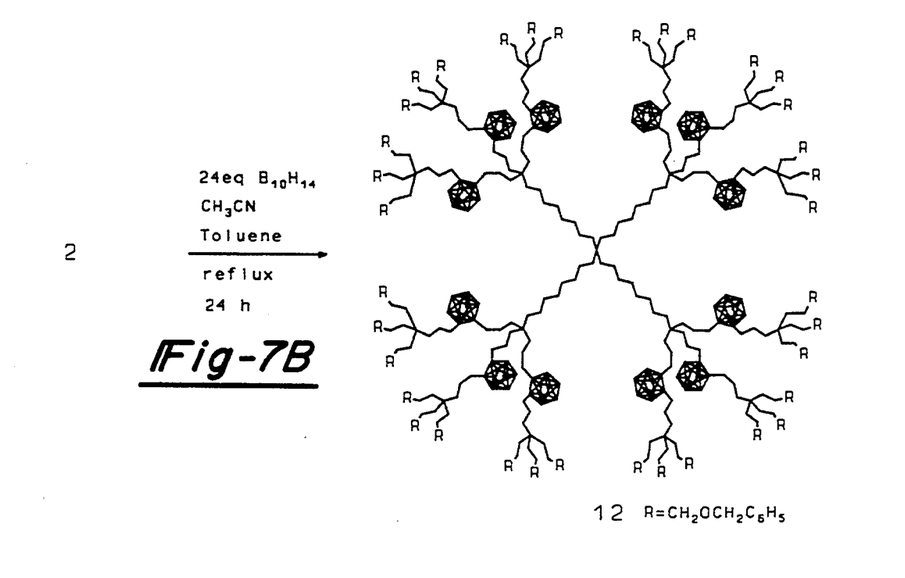

Initial investigations of cascade-based, boron superclusters has focused on the successful synthesis of the tetrakis(o-carborane)[45] (Formula 11) via treatment of the polyalkyne monomer Formula 1 (FIG. 7) with acetonitrile activated decaborane. Similarly, treatment of the dodecaalkyne cascade (Formula 2) with decaborane yielded the dodeca-ocarborane (Formula 12). Evidence for the formation of Formulas 11 and 12 included the disappearance of $^{13}C$ NMR peaks at 80.1 (C≡C) and 19.3 ppm ($CH_2C$≡C) and the appearance of a peak at 29.5 ppm ($CH_2C_2B_{10}H_{10}$). The $^1H$ NMR spectrum exhibited a sharp, intense peak at 2.51 ppm ($B_{10}H_{10}$) postulated to arise by the rapid rate of quadruple relaxation in boron.[46] The exceptional stability of carboranes is employed to obtain supercluster water-solubility. Thus, hydrogenolysis of the benzyl ether moieties (Pd-C) followed by oxidation of the terminal alcohols ($CrO_3$,$H_2SO_4$) to carboxylic acid groups affords the requisite solubilizing terminal moieties after treatment with base. Third and fourth tier cascade intermediates, when subjected to the same procedures, would afford water-soluble superclusters possessing 36 and 108 o-carborane clusters, respectively.

Figure 8A:
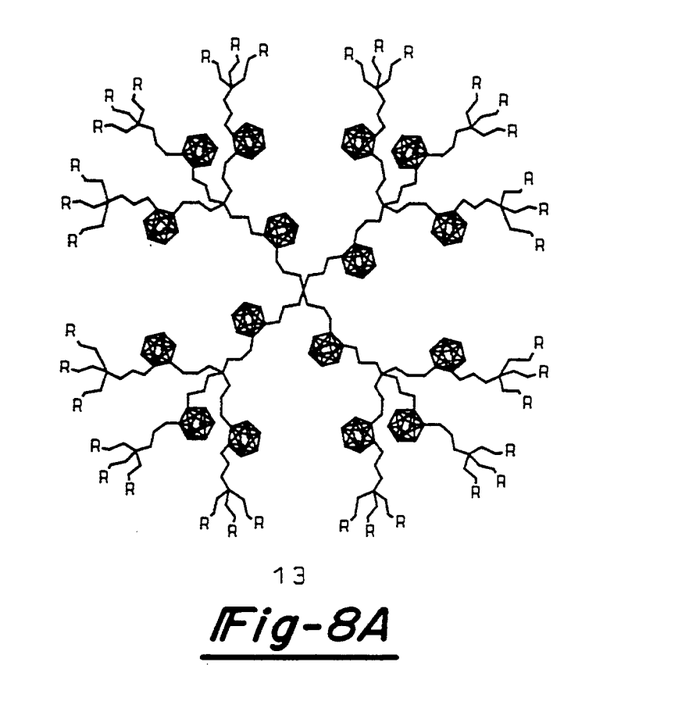
FIG. 8A shows the layering of tiers of the unimolecular Carboranomicelle possessing greater than four internal carborane units.
Figure 8B:
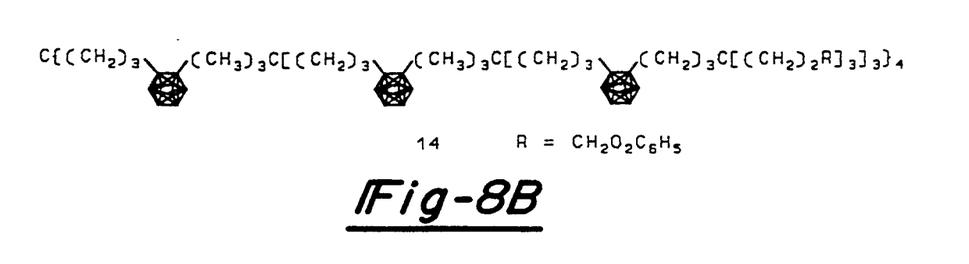
FIG. 8B illustrates the ease of preparation of combinations of multiple (non)metallo sites feasible by the noted tier construction methodology of these unimolecular micelles.

Alternatively, carborane superclusters are prepared wherein each tier or layer of monomer added is treated with decaborane to provide a maximum amount of o-carborane groups within the internal Micellane environment. Thus, second and third generation cascades (Formulas 13 and 14) possess 16 and 52 o-carborane moieties, respectively (FIG. 8).

E. Characterization

Proof of structure is ascertained by NMR spectroscopy.[5] The inclusion of these anisotropic centers within the lyophilic core facilitates NMR studies of included guest(s) moieties and their immediate environment. These data afford insight to the degree of inclusion (penetration) within spherical (Hartley model) micelles. Electron microscopy is used to visually demonstrate the size and shape of the product(s). Since these spherical medio/macromolecules swell and contract under varying solvent and pH conditions,[25] controlled access to these inner metal loci is achieved under very rigid conditions. The introduction of appropriate guests to these potentially catalytic sites is realized in an aqueous environment, since non-porotic guests favor these lipophilic inner regions. The synthesis, characterization, and chemistry of water-soluble unimolecular metallomicelles and metalloidomicelles possessing inner lipophilic pockets containing metal catalytic sites are herein disclosed.

The above examples demonstrate the ability of the present invention to fill void regions by chemical means within dendritic macromolecules. As additional layers are added, constraint will then be imposed at the onset of surface "dense packing" in these dendritic systems. The chemistry of the present invention utilizes inter- and intra-molecular host-guest interactions, as well as chemical transformations at a pre-determined depth within the specific micellar environment. Accordingly, the present invention provides means of utilizing not only the exterior of the micelle for interaction with this environment, but also the lipophilic interior of the unimolecular micelle. These modifications allow for reaction of the micelles in a dramatic fashion with the surrounding environment. The surrounding environment, physiologically, can be drastically modified by such an inter-relationship. Such modification can be medicinal in nature, the micelles providing a pharmacological delivery mechanism.

The invention has been described in an illustrative manner, and it is to be understood the terminology used is intended to be in the nature of description rather than of limitation.

Obviously many modifications and variations of the present invention are possible in light of the above teachings. Therefore, it is to be understood that within the scope of the appended claims, the invention may be practiced otherwise than as specifically described.

REFERENCES 1. (a) Mittal, K. et al. in *Micellization, Solubilization, and Microemulsions*, Mittal, K.L., Ed.; Plenum Press, New York, 1977;

(b) Tanford, C. in *The Hydrophobic Effect: The Formation of Micelles and Biological Membranes*, 2nd Ed., Wiley-Interscience, New York, 1980;

(c) Ringsdorf, H. et al., *Angew. Chem. Int. Ed. Engl,* 1988, 27, 113.

2. Menger, F. *Angew. Chem. Int. Ed. Engl.* 1991, 30, 1086.

3. (a) Mekelburger, H., Jaworek, W., Vögtle, F. *Angew. Chem. Int. Ed, Engl,* 1992, 31, 1571

(b) Buhlin, E., Wehner, W., Vögtle, F., *Synthesis,* 1978, 155

4. Newkome, G. R., Moorefield, C. N., Baker, G. R. *Adrichimca Acta* 1992, 25, 31.

5. Newkome, G. R., Moorefield, C. N., Baker, G. R., Johnson, A. L., Behera, R. K. *Angew Chem. Int. Ed. Engl.,* 1991, 30, 1176.

6. Newkome, G. R., Moorefield, C. N., Baker, G. R., Saunders, M. J., Grossman, S. H. *Angew Chem. Int. Ed. Encl.* 1991, 30, 1178.

7. (a) Tomalia, D. A., et al., *Marcromoecules* 1987, 20, 1167;

(b) Tomalia, D. A., et al., *Macromolecules* 1986, 19, 2466; Tomalia, D. A., et al., *J. Am. Chem. Soc.* 1987, 109, 1601.

8. Pessi, A., Bianchi, E., Bonelli, F. Chiappinelli, L. J, *Chem. Soc., Chem. Commun.* 1990, 8.

9. Padias, A. B., Hall, H. K. Jr., Tomalia, D. A., McConnell, J. R. *J. Org. Chem.* 1987, 52, 5305.

10. Bochkov, A. F., et al., *Izv, Akad. Nauk SSSR, Ser. Khim.* 1989, 2395.

11. Rengan, K., et al. *J. Chem. Soc., Chem. Commum.* 1990, 1084.

12. Uchida, H., et al., *J. Am. Chem. Soc.* 1990, 112, 7077.

13. Bochkarev, M. N., et al., *J. Organomet. Chem. (USSR)* 1987, 195.

14. Wooley, K. L., et al., *J. Chem. Soc. Perkin Trans.* 1 1991, 1059; Hawker, C. J., Frechet, J. M. J. *J. Am. Chem. Soc.* 1990, 112, 7638; *Macromolecules* 1990, 23, 4276; *J. Chem. Soc., Chem. Commum.* 1990, 1010.

15. Rajca, A. J. Org. Chem. 1991, 56, 2557; *J. Am. Chem. Soc.* 1990, 5890, 5889.

16. Kim, Y. H., Webster, O. W. *J. Am. Chem. Soc.* 1990, 112, 4592.

17. Miller, T. M., Neenan, T. X. *Chem. Mater.* 1990, 2, 346.

18. Shahlai, K., Hart, H. *J. Am. Chem. Soc.* 1990, 112, 3687; *J. Org. Chem.* 1990, 55, 3412.

19. Moore, J. S., Xu, Z. *Macromolecules* 1991, 24, 5893.

20. Lakowicz, J. R., Cherek, H., Maliwal, B. P. *Biochem.* 195, 24, 376.

21. Shinkai, S., et al., *J. Am. Chem. Soc.* 1986, 108, 2409; Brooker, L. G. S., Sprague, M. H. *J. Am. Chem. Soc.* 1941, 63, 3214.

22. Menger, F. M. Takeshita, M., Chow, J. F. *J. Am. Chem. Soc.* 1981, 103, 5938.

23. Saunders, M. J., et al., *Planta* 1981, 152, 272.

24. Menger, F. M., Takeshita, M., Chow, J. F. *J. Am. Chem. Soc.* 1981, 103, 5938.

25. Newkome, G. R., et al., *Macromolecules* 1993, in press.

26. de Gennes,, P.-G., et al., *J. Phys. Lett.* 1983, 44, 351.

27. Schore, N. E., *Chemical Reviews* 1988, 88, 1081.

28. March, J., *Adv. Org. Chem.*, 1985, 3rd Ed.,

29. Newkome, G. R., Moorefield, C. N. *Polymer Preprints* 1993, 34, 75 (Abstr).

30. Newkome, G. R. et al., Unpublished results (1993)

31. Nicolas, K. M. et al., in "Transition Metal Organometallics in Organic Synthesis", Vol. II, Alper, ed., Academic Press, N.Y. (1978)

32. Nicolaou, K. C. et al., *Am. Chem. Soc.* 113:3106 (1991)

33. Nicholas, K. M. et al., *Tetrahedron Lett.*, 3475 (1971)

34. (a) Exon, C. et al., *J. Am. Chem. Soc.*, 105:2477 (1983)

(b) Knudsen, M. J. et al., *J. Org. Chem.*, 49:5025 (1984)

(c) Magnus, P. et al., *J. Am. Chem. Soc.*, 110:6921 (1988)

(d) Nicholas, K. Acct. *Chem. Res.* 20:207 (1987)

35. Newkome, G. R. et al., in "Contemporary Heterocyclic Chemistry", *Wiley-Interscience, New York* (1982)

36. Distances were determined from extended conformations of modeled Micellanes using Quanta molecular modeling software from Polygen Corp.

37. Newkome, G. R. et al., *J, Am. Chem. Soc.*, 74:671 (1974)

38. Bradley, J. S. et al., *J. Am. Chem. Soc.*, 113:4016 (1991)

39. (a) Kauffman et al., *Am. Chem. Ber.* 109:3864 (1976)

(b) Newkome, G. R. et al., *J. Org. Chem*, 47:4116 (1982)

(c) Pilper, P. J., *The Eur. J. Med. Chem. Chim. Ther.*, p. 399 (1984)

40. Newkome, G. R. et al., *J. Organometal. Chem.*, 198: 225 (1980)

41. Newkome, G. R., *J. Org. Chem.*, 54:5105 (1989)

42. Lee, H. W., Dissertation, Louisiana State University (1983)

43. Tomasik, P. et al., in "Pyridine Metal Complexes", *The Chemistry of Heterocyclic Compounds*, Part 6A–C, *Interscience*, Newkome and Strekowski, editors, New York (1985)

44. (a) Ketz, H. et al., *Tetrahedron Lett.*, 31:4003 (1990)

(b) Mirua, M. et al., *Tetrahedron Lett*, 31:2247 (1990)

(c) Nemoto H. et al., *J. Org. Chem.* 57:437 (1992)

45. Newkome, G. R. et al., *Polymer Preprints*, 1993, 34, 75

46. Akitt, J. W., *J. Mag. Res.*, 1970, 3, 411

What is claimed is:

1. A method of making a cascade polymer includes the steps of
    forming a unimolecular micelle including internal void areas having reactive sites capable of covalent and noncovalent bonding to a guest;
    inclusioning at least one guest in at least one of the void areas;
    bonding at least one guest to a reactive site in a void area; and
    containing the guest(s) within the void area.

2. A method of claim 1 wherein said void areas include a plurality of reactive sites, said method including the step of bonding a plurality of guests within the void areas, thereby forming guest clusters within the unimolecular micelle.

3. A method of claim 2 wherein the unimolecular micelle includes a plurality of tiers, said method further including the step of bonding the guest(s) to reactive sites on a single tier of said micelle.

4. A method of claim 3 further including the steps of bonding a different ligand to a different tier of said unimolecular micelles.

5. A method of claim 1 wherein said inclusioning steps is further defined as expanding said unimolecular micelle to allow access of the guest(s) to the reactive sites, bonding the guest(s) to the reactive sites and contracting the micelle to contain and protect the guest(s).

6. A method of claim 5 wherein the unimolecular micelle is in an environment and has an outer surface which is insoluble in the environment, said expanding step being further defined as changing the environment to increase the solubility of the outer surface of the micelle in the unimolecular environment.

7. A method of claim 6 wherein the unimolecular micelle is in an environment having a pH causing contraction of the micelle by decreasing the solubility of the outer surface of the unimolecular micelle in the environment, said expanding step being further defined as changing the pH of the environment containing the unimolecular micelle to increase the solubility of the outer surface of the unimolecular micelle in the environment; said contracting step being defined as returning the pH back to the original pH of the environment.

8. A method of claim 1 wherein the unimolecular micelle includes arms having alkyne moieties, said bonding step being further characterized as treating the alkyne moieties with a metallocarbonyl in an aprotic solvent, the metallo addition complexed to the internal ligand site(s).

9. A method of claim 8 wherein the metal of the metallo moiety is selected from the group including, cobalt, platinum, copper, palladium, ruthenium, osmium, iron, rhodium, iridium, nickel, silver, and gold.

10. A method of claim 8 wherein the aprotic solvent is selected from the group including $CH_2Cl_2$, $HCCl_3$, $CCl_4$, R—O—R' wherein R and R' are selected from the group consisting of aralkyl and aryl groups, $C_6H_6$ and $CH_3C_6H_5$.

11. A method of claim 1 wherein the unimolecular micelle includes arms having polyalkyne moieties, said bonding step being further defined as bonding a zero-valent metal under reductive conditions and in the presence of a phosphine donor to the alkyne moieties and thermolysing the phosphine to generate the zero-valent metal trapped within the void area of the unimolecular micelle.

12. A method of claim 1 wherein the micelle includes arms having bidentate diamino chelate ligands, said bonding step being further defined as chelating Cu+2 to the ligand.

13. A method of claim 12 wherein said forming step is further defined as alkylating a chloro-terminated monomer of the formula:

wherein R=CH$_2$OR'CO$_2$R", CN, and CH$_2$NR$_2$''', R'=Me, CH$_2$C$_6$H$_5$; (R"=Me, Et, pr, bu(t), CH$_2$Aryl and R'''=H, alkyl, aryl, and alkyonyl with (2,3, or 4-lithiomethyl-2',3' or 4'-methyl) bipyridine to form the bidentate diamino of the formula selected from the group consisting of:

a)

-continued b)

c)

and d)

14. A method of claim 13 further including the subsequent steps of lithiating of terminal methyl groups and adding further polyhalides to form further internal bidentate loci in void areas of the unimolecular micelle.

15. A method of claim 1 wherein the unimolecular micelle includes arms having polyalkyne moieties, said bonding step being further defined as treating the alkyne moiety with acetonitrile activated decarborane to form a carborane moiety.

* * * * *